United States Patent [19]

Shiokawa et al.

[11] Patent Number: 4,647,570
[45] Date of Patent: Mar. 3, 1987

[54] PESTICIDAL NOVEL NITROMETHYLENE DERIVATIVES

[75] Inventors: Kozo Shiokawa, Kanagawa; Shinichi Tsuboi, Tokyo; Shinzo Kagabu, Tokyo; Koichi Moriya, Tokyo, all of Japan

[73] Assignee: Nihon Tokushu Noyaku Seizo K.K., Tokyo, Japan

[21] Appl. No.: 699,756

[22] Filed: Feb. 8, 1985

[30] Foreign Application Priority Data

Feb. 16, 1984 [JP] Japan ................................. 59-26020

[51] Int. Cl.$^4$ .................. C07D 401/06; A61K 31/415
[52] U.S. Cl. .................................. 514/341; 546/278; 544/335; 514/218; 514/256; 540/553
[58] Field of Search .......................... 546/278; 514/341

[56] References Cited

U.S. PATENT DOCUMENTS 3,971,774 7/1976 Tieman et al. .
4,002,765 1/1977 Tieman et al. .

FOREIGN PATENT DOCUMENTS 2514402 10/1976 Fed. Rep. of Germany .
2732660 2/1979 Fed. Rep. of Germany .
2014147 8/1979 United Kingdom .

OTHER PUBLICATIONS

Chemical Abstracts, vol. 90, 1979, p. 522, Abstract 86292q, Pyrimidines.

Primary Examiner—Jane T. Fan
Attorney, Agent, or Firm—Sprung Horn Kramer & Woods

[57] ABSTRACT

A pesticidal nitromethylene derivative of the formula

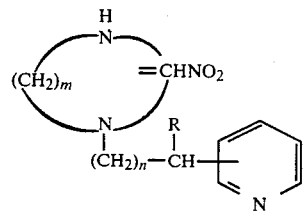

in which
R is a hydrogen atom or a lower alkyl group,
m is 2, 3 or 4, and
n is 0, 1, 2 or 3,
is produced by reacting a compound of the formula

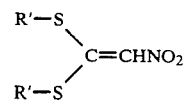

in which
R' each independently is a lower alkyl group, or together are an alkylene group forming a ring with the adjoining sulfur atoms.

6 Claims, No Drawings

PESTICIDAL NOVEL NITROMETHYLENE DERIVATIVES

This invention relates to novel nitromethylene derivatives, a process for production thereof, and an insecticidal, miticidal and nematocidal agent.

More specifically, this invention relates to novel nitromethylene derivatives represented by the following general formula (I).

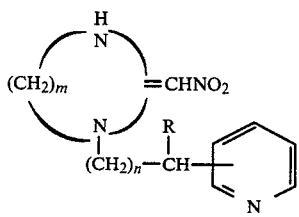

wherein R represents a hydrogen atom or a lower alkyl group, m represents 2, 3 or 4, and n represents 0, 1, 2 or 3.

The nitromethylene derivatives of formula (I) in accordance with this invention can be produced by the following process (i) to which the invention also pertains.

Process (i)

A process for producing the nitromethylene derivatives of general formula (I), which comprises reacting a compound represented by the general formula

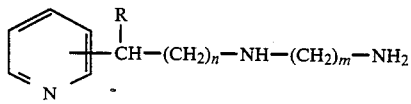

wherein R, m and n are as defined above,
with a compound represented by the general formula

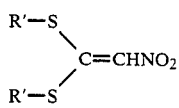

wherein each R' represents a lower alkyl group, or the two R' groups together represent a lower alkylene group having at least 2 carbon atoms and may form a ring together with the sulfur atoms adjacent thereto.

Furthermore, this invention relates to an insecticidal, miticidal and nematocidal agent comprising the nitromethylene derivative of general formula (I) as an active ingredient.

German Offenlegungsschrift No. 2,514,402 known before the filing date of the present application states that 2-nitromethylene-imidazolidine derivatives and 2-nitromethylene-hexahydropyrimidine derivatives of the general formula

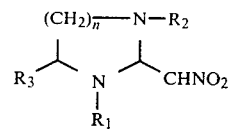

have insecticidal activity. The above general formula includes cases of n=2, R$_1$=phenyl-(C$_1$-C$_2$)alkyl group and R$_2$=R$_3$=hydrogen and the specification of the above German patent document describes a compound of the formula

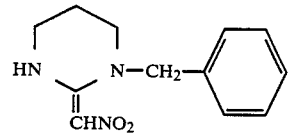

German Offenlegungsschrift No. 2,732,660 states that 1-substituted benzyl-2-nitromethyleneimidazolidine derivatives of the formula

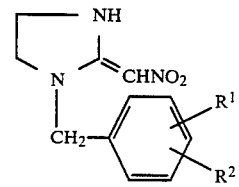

have insecticidal activity. The specification of this German Offenlegungsschrift describes a compound represented of the formula

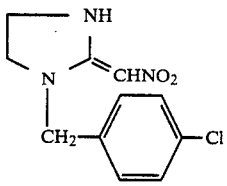

In order to create novel useful compounds having biological activity, the present inventors synthesized nitromethylene-tetrahydropyrimidine compounds and nitromethylene-imidazolidine compounds and performed biological screening on these compounds. As a result, the present inventors have now succeeded in synthesizing the nitromethylene derivatives of general formula (I) not described in the prior known literature, and have found that these compounds possess outstanding controlling activity against noxious insects, mites and nematodes.

In the chemical structures of the novel compounds, 2-nitromethylene-tetrahydropyrimidine, 2-nitromethylene-imidazolidine, or 2-nitromethylene-hexahydro-1,3-diazepine constitutes a basic skeleton, and as is clearly seen from the general formula (I), a pyridylalkyl group is substituted at the nitrogen atom at the 1-position of the aforesaid hetero ring. Unexpectedly, it has been found that there is a correlation between this chemical structure and the exhibition of high activity (controlling activity) by the compounds of formula (I). In addition, it has been found that when the pyridyl alkyl group is specifically a 3-pyridylmethyl group or 4-pyridylmethyl group, an especially superior correlation is established.

It has also been found that the compounds of this invention in low dosages have quite outstanding controlling activity over the compounds of formulae (A-1) and (B-1) which are described in the above-cited German Offenlegungsschriften and are most similar to the compounds of this invention, and that the compounds of this invention exhibit a marked controlling effect against noxious insects which have acquired resistance to organic phosphate and carbamate type insecticides through long-term use, particularly sucking insects typified by hemipterous insects such as aphids. planthoppers and leafhoppers.

The active compounds of this invention exhibit an accurate controlling effect against noxious insects, mites or ticks, and nematodes without causing any phytotoxicity to cultivated plants. Futhermore, the compounds of this invention can be used for control and eradication of a wide range of pests, including sucking insects, biting insects and other plant parasites, pests on stored grains and pests causing health hazards.

Examples of the pests are shown below.

Coleopterous Insects

*Callosobruchus chinensis,*
*Sitophilus zeamais,*
*Tribolium castaneum,*
*Epilachna vigitioctomaculata,*
*Agriotes fuscicollis,*
*Anomala rufocuprea,*
*Leptinotarsa decemkineata,*
Diabrotica spp.,
*Monochamus alternatus,*
*Lissorhoptrus oryzophilus,* and
*Lyctus brunneus.*

Lepidopterous Insects

*Lymantria dispar,*
*Malacosoma neustria,*
*Pieris rapae,*
*Spodoptera litura,*
*Mamestra brassicae,*
*Chilo suppressalis,*
*Pyrausta nubilalis,*
*Ephestia cautella,*
*Adoxophyes orana,*
*Carpocapsa pomonella,*
*Agrotis fucosa,*
*Galleria mellonella,*
*Plutelly maculipennis,* and
*Phyllocnistis citrella.*

Hemipterous Insects

*Nephotettix cincticeps,*
*Nilaparvata lugens,*
*Pseudococcus cometocki,*
*Unasis yanonensis,*
*Myzus persicae,*
*Aphis pomi,*
*Aphis gossypii,*
*Rhopalosiphum pseudobrassicas,*
*Stephanitis nashi,*
Nazara spp.,
*Cimex lectularius,*
*Trialeurodes vapariourum,* and
Psylla spp.

Orthopterous Insects

*Blatella germanica,*
*Periplaneta americana,*
*Gryllotalpa africana,* and
*Locusta migratoria migratoriodes.*

Isopterous Insects

*Deucotermes speratus,* and
*Coptotermes formosanus.*

Dipterous Insects

*Musca domestica,*
*Aedes aegypti,*
Hylemia platura,
*Culex pipens,*
*Anopheles sinensis,* and
*Culex tritaeniorhynchus.*

Mites

*Tetranyhus telarius,*
*Panonychus citri,*
*Aculus pelekassi,* and
Tnrronomus spp.

Nematodes

*Meloidogyne incognita,*
*Bursaphelenchus lignicolus Mamiga et Kiyohara,*
*Aphelenchoides besseyi,*
*Beterodera glycines,* and
Pratylenchus spp.

In the field of veterinary medicine, the novel compounds of this invention are effective against various noxious animal parasites (endo- and ecto-parasites) such as ticks, insects and worms. Examples of such animal parasites are shown below.

Ticks

Oranithodoros spp,
Ixodes spp., and
Boophilus spp.

Insects

Gastrophilus spp.,
Stomoxys spp.,
Trichodectes spp.,
Rhodnius spp., and
*Ctenocephalides canis.*

Substances having pesticidal activity against all of these pests may sometimes be referred to in this application simply as insecticides.

The nitromethylene derivative of general formula (I) in accordance with this invention can be easily produced, for example, by the following process (i):

Process (i)

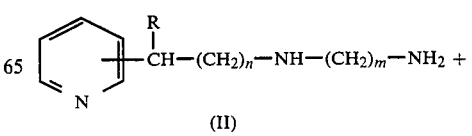

$$\text{CH}-(\text{CH}_2)_n-\text{NH}-(\text{CH}_2)_m-\text{NH}_2 +$$

(II)

-continued
Process (i)

$$R'-S\diagdown \atop R'-S\diagup C=CHNO_2 \longrightarrow$$

(III)

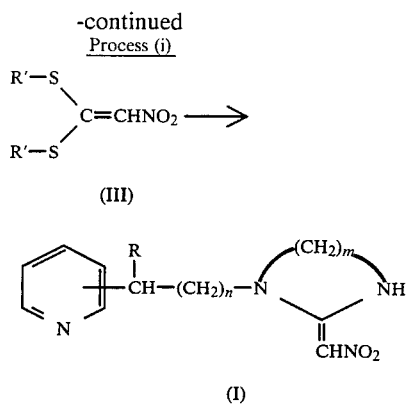

(I)

(In the formulae, R, m, n and R' are as defined hereinabove.)

In the above reaction scheme, R represents a hydrogen atom or a lower alkyl group, and specific examples may include methyl, ethyl, propyl, isopropyl and n-(iso-, sec- or tert-)butyl. m represents 2, 3 or 4, and n represents 0, 1, 2 or 3. R' represents a lower alkyl group, or the two R' groups together represent a lower alkylene group having at least 2 carbon atoms. Specific examples of the lower alkyl group are the same as those exemplified above for R. The two R' groups together represent a lower alkylene group having at least 2 carbon atoms and may form a ring together with the sulfur atoms adjacent thereto. An ethylene group may be cited as an example of such an alkylene group.

In the process for producing the compounds of general formula (I) of this invention represented by the reaction scheme, specific examples of the starting compound of general formula (II) include N-(2-pyridylmethyl)ethylenediamine,
N-(3-pyridylmethyl)ethylenediamine,
N-(4-pyridylmethyl)ethylenediamine,
N-[2-(4-pyridyl)ethyl]ethylenediamine,
N-(2-pyridylmethyl)trimethylenediamine,
N-[2-(2-pyridyl)ethyl]trimethylenediamine,
N-(3-pyridylmethyl)trimethylenediamine,
N-[1-(3-pyridyl)ethyl]trimethylenediamine,
N-[3-(3-pyridyl)propyl]trimethylenediamine,
N-(4-pyridylmethyl)trimethylenediamine,
N-[1-(4-pyridyl)ethyl]trimethylenediamine,
N-[1-(3-pyridyl)ethyl]ethylenediamine,
N-[1-(4-pyridyl)ethyl]ethylenediamine, and
N-(4-pyridylmethyl)tetramethylenediamine.

Specific examples of the compound of general formula (III) which is likewise a starting material include 1-nitro-2,2-bis(methylthio)ethylene,
1-nitro-2,2-bis(ethylthio)ethylene, and
2-nitromethylene-1,3-dithiolane.

By citing the following typical example, the above process will be specifically described:

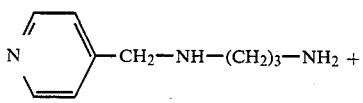

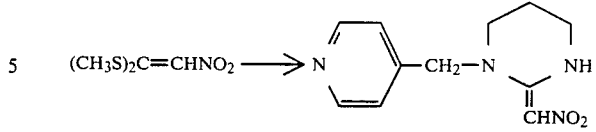

Desirably, the above process for producing the compound of this invention can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above process can be carried out over a wide temperature range. Generally, it can be carried out at a temperature between about $-20°$ C. and the boiling point of the mixture, preferably between about $0°$ C. and about $100°$ C. Desirably, the reaction is carried out under normal atmospheric pressure, but it is also possible to operate under elevated or reduced pressures.

The compound of general formula (I) in accordance with this invention may also be produced by a process (II) schematically shown below.

Process ii (alternative process)

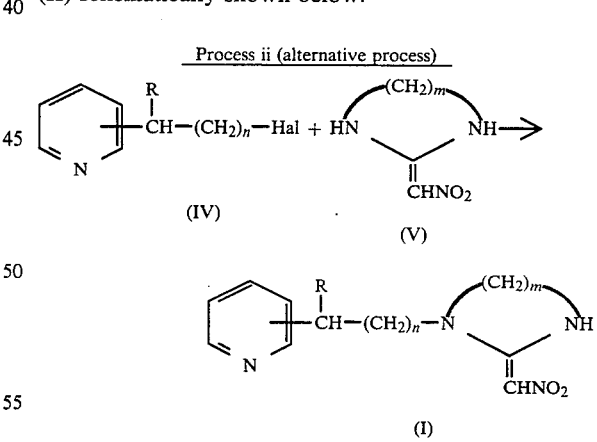

(In the above formulae, R, m and n are as defined hereinabove, and Hal represents a halogen atom.)

In the process for producing the compounds of general formula (I) in accordance with this invention, specific examples of the compounds of general formula (IV) which is a starting material are 3-pyridylmethyl chloride, 4-pyridylmethyl chloride and 2-pyridylmethyl chloride. The corresponding bromides may also be cited. Specific examples of the compound of general formula (V) which is likewise a starting material include 2-nitromethylene-imidazolidine, 2-nitromethylene-tetrahydropyrimidine and 2-nitromethylene-hexahydro-1,3-diazepine.

By citing the following referential example, the process (ii) will be specifically described:

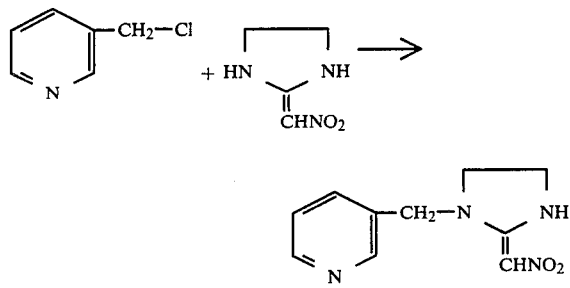

The above process can be carried out by using the same inert solvents or diluents as exemplified for the process (i).

The above reaction may be carried out in the presence of an acid binder. Examples of the acid binder are the hydroxides, carbonates, bicarbonates and alcoholates of alkali metals, and tertiary amines such as triethylamine, diethylaniline and pyridine, which are generally used.

As is the case with the process (i), the above process can be carried out over a wide temperature range. The reaction is carried out desirably under normal atmospheric pressure, but it is also possible to operate under elevated or reduced pressure.

The compounds of this invention may be present in the form of salts. The salts may, for example, be inorganic salts, sulfonates, organic acid salts, and metal salts. Specific examples of the compounds of this invention in the form of salts include 1-(3-pyridylmethyl)-2-(nitromethylene)tetrahydropyrimidine hydrochloride,
1-(4-pyridylmethyl)-2-(nitromethylene)tetrahydropyrimidine hydrochloride,
1-(4-pyridylmethyl)-2-(nitromethylene)imidazolidine hydrochloride,
1-(3-pyridylmethyl)-2-(nitromethylene)imidazolidine hydrochloride,
1-(4-pyridylmethyl)-2-(nitromethylene)tetrahydropyrimidine p-toluenesulfonate,
1-(4-pyridylmethyl)-2-(nitromethylene)tetrahydropyrimidine succinate, and
1-(4-pyridylmethyl)-2-(nitromethylene)tetrahydropyrimidine cupric acetate.

As an insecticidal, miticidal and nematocidal agent, the compounds of this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents, stabilizers, stickers, aerosol propellants and synergists.

Examples of the solvents are water, and organic solvents, for example hydrocarbons [such as n-hexane, petroleum ether, petroleum fractions (e.g., paraffin waxes, kerosene, light oils, middle oils, and heafy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acid (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chlorides) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoromethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, pulverulent preparations, fumigants, tablets, aerosols, pastes and capsules.

The insecticidal, miticidal and nematocidal agent of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of noxious insects, mites or ticks, and nematodes.

If required, the compounds of this invention may be used in combination with other agricultural chemicals, for example other insecticides, fungicides, other miticides, other nematocides, antiviral agents, herbicides, plant growth regulators and attractants (such as organophosphate compounds, carbamate compounds, dithio (or thiol) carbamate compounds, organochlorine compounds, dinitro compounds, organosulfur or organometallic compounds, antibiotics, substituted diphenyl ether compounds urea compounds, and triazine compounds), and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); fumigation; soil application (mixing, sprinkling, vaporing, pouring, etc.); surface application (coating, banding power coating, covering, etc.); dipping; and baiting. It can also be used by the so-called ultralow volume spraying method. According to this method, the active ingredient may be included in an amount of 100%.

The rate of application per unit area is, for example, about 0.03 to about 10 kg, preferably about 0.3 to about 6 kg, per hectare. In special cases, however, it may, and sometimes should, be outside the specified range.

According to this invention, there can be provided an insecticidal, miticidal and nematocidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling noxious insects, mites or ticks, and nematodes, which comprises applying to a noxious insect, mite or tick, or nematode and/or its habitat or the locus of its occurrence the compound of general formula (I) alone or in admixture with a diluent (a solvent and/or an extender and/or a carrier) and/or a surface-active agent and if further required, a stabilizer, a sticker, a synergist, etc.

The following examples illustrates the present invention specifically. It should be noted however that the invention is not limited to these specific examples alone.

EXAMPLE 1

A mixture of N-(4-pyridylmethyl)trimethylenediamine (16.5 g), 1-nitro-2,2-bis(methylthio)ethylene (16.5 g) and methanol (100 ml) was refluxed for 2 hours with stirring. The generated gas was collected by an alkali trap. The reaction mixture was cooled to room temperature, and the resulting crystals were filtered to give 1-(4-pyridylmethyl)-2-(nitromethylene)tetrahydropyrimidine (16 g) of the following formulas as pale yellow crystals. Concentrating the filtrate further gave 3 g of this compound. mp. 226°–228° C.

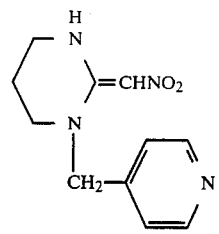
(Compound No. 1)

EXAMPLE 2

A mixture of N-(3-pyridylmethyl)ethylenediamine (15.1 g), 1-nitro-2,2-bis(methylthio)ethylene (18.2 g) and benzene (150 ml) was refluxed for 4 hours with stirring. The generated gas was collected by an alkali trap. The reaction mixture was cooled to room temperature, and filtered to collect crystals. Recrystallization from methanol gave 1-(3-pyridylmethyl)-2-(nitromethylene imidazolidine (17 g) of the following formula as pale yellow crystals. mp. 169°–171° C.

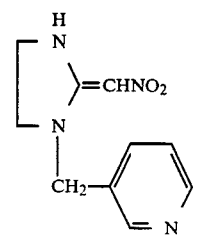
(Compound No. 2)

Table 1 below shows the compounds of this invention which were synthesized in much the same way as in Examples 1 and 2.

TABLE 1

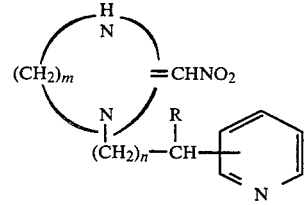

| Compound No. | R | m | n | Pyridine-bonded position | Physical constant |
|---|---|---|---|---|---|
| 3 | H | 2 | 0 | 2- | mp. 209–212° C. |
| 4 | H | 2 | 0 | 4- | mp. 203–206° C. |
| 5 | H | 2 | 1 | 4- | mp. 219–221° C. |
| 6 | H | 3 | 0 | 2- | mp. 202–203° C. |
| 7 | H | 3 | 1 | 2- | mp. 105–108° C. |
| 8 | H | 3 | 0 | 3- | mp. 207–209° C. |
| 9 | —CH$_3$ | 3 | 0 | 3- | mp. 171–172° C. |
| 10 | H | 3 | 2 | 3- | mp. 137–140° C. |
| 11 | —CH$_3$ | 3 | 0 | 4- | mp. 222–225° C. |
| 12 | —CH$_3$ | 2 | 0 | 3- | mp. 121–122° C. |
| 13 | —CH$_3$ | 2 | 0 | 4- | mp. 189–190° C. |
| 14 | H | 4 | 0 | 4- | |
| 15 | —C$_2$H$_5$ | 2 | 0 | 4- | |
| 16 | —C$_3$H$_7$—iso | 3 | 0 | 3- | |
| 17 | —C$_3$H$_7$—iso | 3 | 0 | 4- | |
| 18 | —CH$_3$ | 2 | 1 | 3- | |
| 19 | —C$_2$H$_5$ | 2 | 0 | 3- | |

Specific examples of salts of the aforesaid compounds of this invention are shown below.

EXAMPLE 3

1-(4-Pyrdylmethyl)-2-(nitromethylene)tetrahydropyrimidine (0.74 g) obtained in Example 1 was dissolved in ethanol (20 ml), and concentrated hydrochloric acid (2 ml) was added. The reaction mixture was stirred at room temperature for 24 hours. The precipitated crystals were collected by filtration, and washed fully with ether to give the hydrochloride (0.72 g) of compound No. 1 of this invention. mp. 185° C. (decomp.).

EXAMPLE 4

Compound No. 1 (0.73 g) obtained in Example 1 was dissolved in a mixed solvent of acetone (10 ml) and chloroform (50 ml), and p-toluenesulfonic acid hydrate (0.63 g) was added. The mixture was vigorously shaken for 2 hours, and then allowed to stand at room temperature for 3 hour. The precipitated crystals were collected by filtration, and fully washed with acetone to give the p-toluenesulfonate (1.2 g) of compound No. 1 of this invention. mp. 170°-176° C.

EXAMPLE 5

Compound No. 1 (0.74 g) obtained in Example 1 was dissolved in anhydrous ethanol (50 ml), and cupric acetate (0.665 g) was added. The reaction mixture was stored at room temperature for about 24 hours, and then filtered. The resulting pale green solid was washed with a small amount of water and then well with chloroform, and finally dried in vacuum to give the copper salt (1.15 g) of compound No. 1 of the invention. mp. 220°-225° C. (decomp.).

Table 2 shows the aforesaid salts of the compound of this invention, and another example of the salt (organic acid salt).

TABLE 2

| Compound No. | Formula | Physical constant |
|---|---|---|
| 1-a | 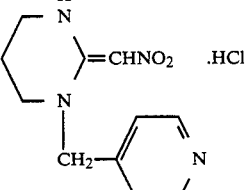 | described in Example 3 |
| 1-b | 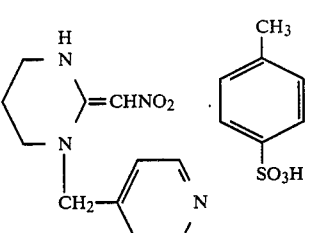 | described in Example 4 |
| 1-c | 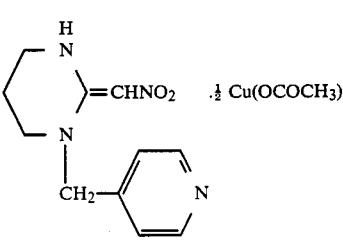 | described in Example 5 |
| 1-d | 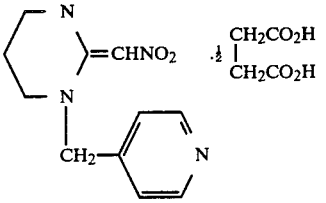 | mp. 180–185° C. |

EXAMPLE 6 (WETTABLE POWDER)

Fifteen parts of compound No. 4 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a noxious insect, mite or nematode and/or its habitat or the locus of its occurrence.

EXAMPLE 7 (EMULSIFIABLE CONCENTRATE)

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a noxious insect, mite or nematode and/or its habitat or the locus of its occurrence.

EXAMPLE 8 (DUST)

Two parts of compound No. 1 of the invention and 98 parts of powdery clay are pulverized and mixed to form a dust. It is scattered over a noxious insect, mite or nematode and/or its habitat or the locus of its occurrence.

EXAMPLE 9 (GRANULES)

Water (25 parts) is added to a mixture consisting of 10 parts of compound No. 8 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a noxious insect, mite or nematode and/or its habitat or the locus of its occurrence.

EXAMPLE 10 (GRANULES)

Ninety-five parts of clay mineral particles having a particle size distribution between 0.2 and 2 mm are put in a rotary mixer, and with rotation, 5 parts of compound No. 1 of the invention is sprayed onto the particles to wet them uniformly. The wet mixture is dried at 40° to 50° C. to form granules. The granules are scattered over a noxious insect, mite or nematode and/or its habitat or the locus of its occurrence.

EXAMPLE 11 (OIL PREPARATION)

Compound No. 1 of this invention (0.5 part) and 99.5 parts of kerosene are mixed and stirred to form an oil preparation. It is sprayed onto a noxious insect, mite or nematode and/or its habitat or the locus of its occurrence.

EXAMPLE 12 (BIOLOGICAL TEST)

Test on *Nephotettix cincticeps* having resistance to organophosphorus agents:

Preparation of a Test Chemical

Solvent: 3 parts by weight of xylene
Emulsifier: 1 part by weight of polyoxyethylene alkyl phenyl ether To form a suitable preparation, 1 part by weight of the active compound was mixed with the aforesaid amount of the solvent containing the aforesaid amount of the emulsifier. The mixture was diluted with water to a predetermined concentration.

Testing Method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the kill ratio was calculated.

Against comparison compounds having formulae (A-1) and (B-1) respectively

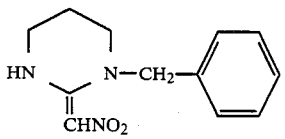
(A-1)

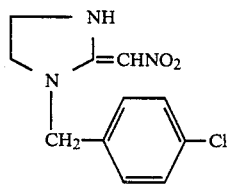
(B-1)

the following compounds according to this invention exhibited unexpected advantages: Compound No. 1, 1-a, 2 and 4.

EXAMPLE 13 (BIOLOGICAL TEST)

Test on planthoppers:

Testing Method

A water dilution in a predetermined concentration of the active compound prepared as in Example 12 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to organophosphorus chemicals were released into the net. The pots were left to stand in a constant temperature chamber and the number of dead insects was examined two days later. The kill ratio was then calculated.

In the same way as above, the kill ratio was calculated in *Sogatella furcifera* Horvath and organophosphorus-resistant *Laodelphax striatellus* Fallen.

Against comparison compound (A-1) and (B-1) the following compounds according to the invention exhibited unexpected advantages: Compound No. 1, 1-a, 1-b, 1-d, 2, 4, 6, 8 and 9.

EXAMPLE 14 (BIOLOGICAL TEST)

Test on *Myzus persicae* (green peach aphids) having resistance to organophosphorus chemicals and carbamate chemicals:

Testing Method

Green peach aphids which had been bred and had resistance to organophosphorus chemicals and carbamate chemicals were inoculated on eggplant seedlings (black elongate eggplants), about 20 cm tall, grown in unglazed pots having a diameter of 15 cm (about 200 aphids per seelding). One day affer the inoculation, a water dilution of each active compound at a predetermined concentration prepared as in Example 12 was sprayed in a sufficient amount onto the plants using a spray gun. After the spraying, the pots were left to stand in a greenhouse at 28° C. Twentyfour hours after the spraying, the kill ratio was calculated. For each compound, the test was carried out through two replicates.

Against comparison compounds A-1 and B-1 and Estox (commercial product) the following compounds according to the invention exhibited unexpected advantages: Compound No. 1, 2 and 8.

It will be appreciated that the instant specification and examples are set forth by way of illustration and not limitation, and that various modifications and changes may be made without departing from the spirit and scope of the present invention.

What is claimed is:

1. A nitromethylene derivative of the formula

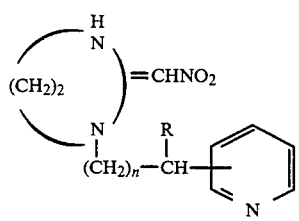

in which

R is a hydrogen atom or a lower alkyl group, and n is 0, 1, 2 or 3, or a salt thereof.

2. A compound according to claim 1, wherein such compound is 1-(3-pyridylmethyl)-2-(nitromethylene)imidazolidine of the formula

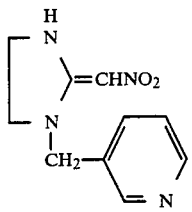

or a salt thereof.

3. A compound according to claim 1, wherein such compound is 1-(4-pyridylmethyl)-2-(nitromethylene)imidazolidine of the formula

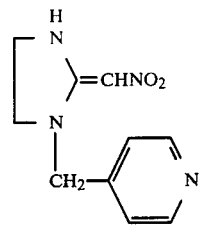

or a salt thereof.

4. An insecticidal, miticidal or nematocidal composition comprising an insecticidally, miticidally or nematocidally effective amount of a nitromethylene derivative or salt thereof according to claim 1 in admixture with a diluent.

5. A method of combating insects, mites or nematodes which comprises applying thereto or to a habitat thereof an insecticidally, miticidally or nematocidally effective amount of a nitromethylene derivative or salt thereof according to claim 1.

6. The method according to claim 5, wherein such compound is
1-(3-pyridylmethyl)-2-(nitromethylene)imidazolidine, or
1-(4-pyridylmethyl)-2-(nitromethylene)imidazolidine, or a salt thereof.

* * * * *